(12) United States Patent
Mall et al.

(10) Patent No.: US 6,376,709 B1
(45) Date of Patent: Apr. 23, 2002

(54) PROCESS FOR THE CRYSTALLIZATION OF DICARBOXYLIC ACIDS

(75) Inventors: Sanjib Mall; Satyanand Chirravuri, both of Pune (IN)

(73) Assignee: Chemintel (India) Private Limited, Gujarat (IN)

( * ) Notice: Subject to any disclaimer, the term of this patent is extended or adjusted under 35 U.S.C. 154(b) by 0 days.

(21) Appl. No.: 09/363,345

(22) Filed: Jul. 28, 1999

(51) Int. Cl.[7] .............................................. C07C 51/42
(52) U.S. Cl. ...................... 562/593; 562/593; 562/530
(58) Field of Search ................. 562/593, 530, 562/543

(56) References Cited

U.S. PATENT DOCUMENTS

| | | | |
|---|---|---|---|
| 3,023,238 A | * | 2/1962 | Chapman et al. |
| 3,102,908 A | * | 9/1963 | Raynes |
| 4,727,218 A | * | 2/1988 | Heiskanen |
| 5,149,867 A | | 9/1992 | Chen et al. ................. 562/486 |
| 5,296,639 A | * | 3/1994 | Klug et al. |
| 5,567,842 A | | 10/1996 | Izumisawa et al. ......... 562/486 |

FOREIGN PATENT DOCUMENTS

EP 0633240 1/1995

* cited by examiner

*Primary Examiner*—Gary Geist
*Assistant Examiner*—Farhad Forohar
(74) *Attorney, Agent, or Firm*—Ladas & Parry

(57) ABSTRACT

The subject invention relates to a process for the crystallization of di-carboxylic acids comprising dissolving the crude dicarboxylic acid at a temperature sufficient to dissolve the crude diacid in the solvent, whereby portion of the said solvent evaporates, increasing the concentration of the dicarboxylic acid in the said solution, transferring the said solution from the evaporator to a crystallizer, comprising a solid cylindrical impeller conforming to the shape of the crystallizer related by means of a cylindrical shaft attached to the spped motor, adding the additives selected from surfactants, buffer salts and/or acid salts or mixture thereof in the said evaporated solution in the said crystallizer, cooling the said mixture resulting in the formation of crystals of dicarboxylic acids, wherein the said crystallization takes place in the annular space between the impeller and the crystallizer wall.

18 Claims, 1 Drawing Sheet

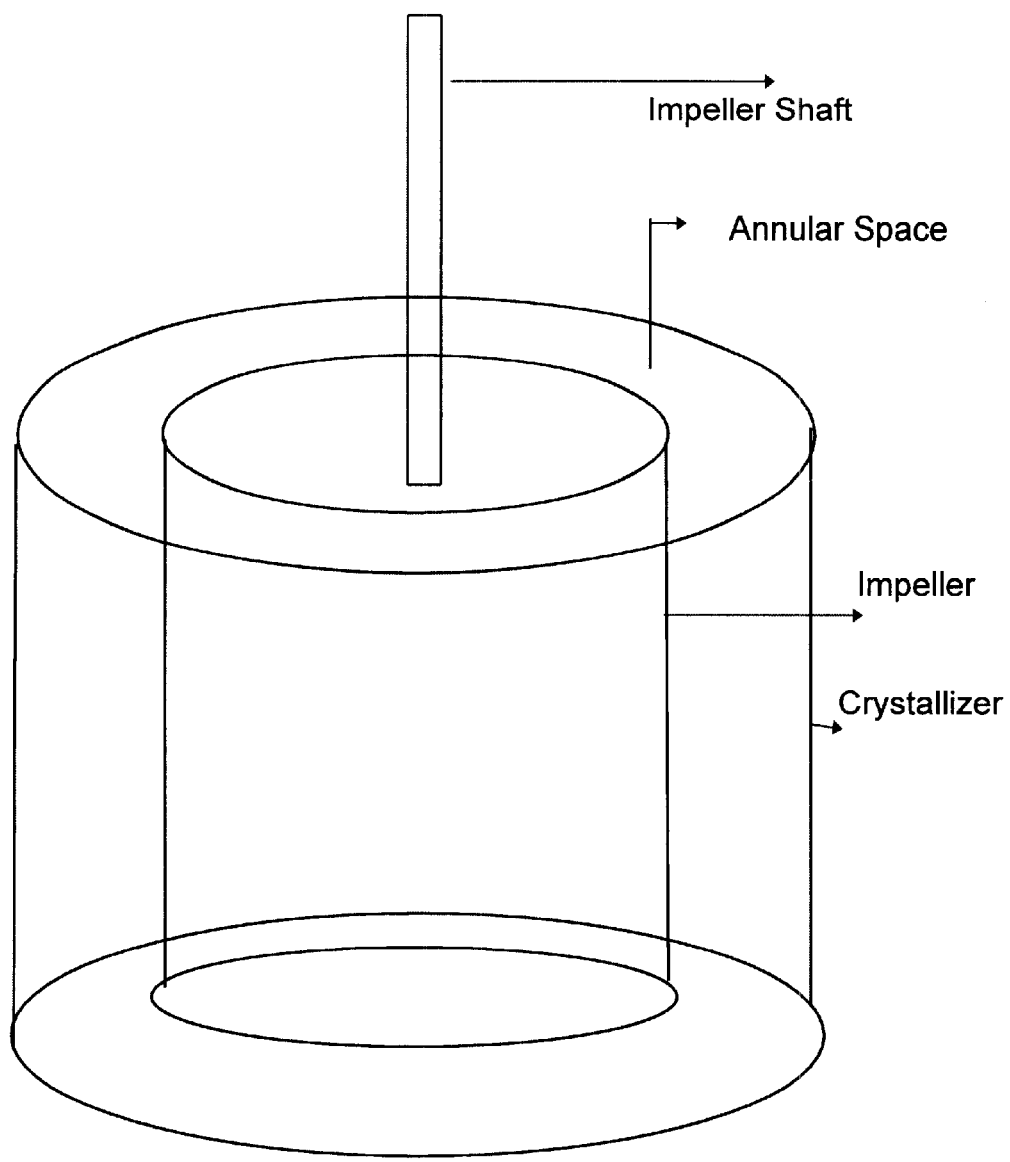

PROCESS FOR THE CRYSTALLIZATION OF DICARBOXYLIC ACIDS

The present invention relates to a process for the crystallization of dicarboxylic acids.

More specifically, the present invention relates to a novel process for the crystallization of dicarboxylic acids employing the use of additives which help increase the yield and purity of crystals.

The object of the invention is to achieve the desired increased size, high purity and greater yield of crystals.

The other object of the invention is to achieve a crystallization process in which crystallization is at a faster rate as compared to the conventionally known processes.

Still another object of the invention is to achieve the desired results by consuming less energy.

The embodiment of the invention resides in the crystallization of di-carboxylic acids in a novel crystallizer comprising a cylindrical impeller and impeller shaft.

Surfactants and/or salts are used as additives to achieve the desired increased size of crystals and high yield.

Addition of surfactants as additives for the crystallization of dicarboxylic acids results in obtaining bigger crystals with high purity, whereas addition of salts as additives for the crystallization of dicarboxylic acids results in the greater yield of crystals.

The addition of surfactants and salts result in obtaining high yield crystals of having bigger crystal size.

BACKGROUND OF THE INVENTION

The modification of the crystal morphology and structure is achieved by introduction of additives which stick on one of the preselected crystal faces thereby inhibiting the growth of the crystal predictably perpendicular to the surface on which they adhere. The size of the crystal structure is drastically varied by carrying out crystallization in electrolyte solutions.

U.S. Pat. No. 5,296,639 claims a process for purification of adipic acid during crystallization by modifying crystal morphology through the introduction of additives which are among caproic acid and surfactants, thereby decreasing the incorporation of impurity on the crystal system.

U.S. Pat. No. 5,827,700 teaches a process of recovery and crystallization of citric acid from impure process stream by introducing very strong salts.

Juetten, in his thesis entitled "The Enhanced Crystallization of Dicarboxylic Acids in Electrolyte Solutions", Michigan State University, 1992, performed crystallization experiments on aqueous solutions using dicarboxylic acids in order to determine by trial-and-error which electrolytes caused "salting out".

One of the major drawbacks associated with the use of salts, either buffer salts or acid salts is the instant precipitation, which results in the smaller size of the crystals. In the subject invention to overcome this drawback, the selection of salts with the surfactants has resulted in achieving the desired crystal size along with better yield of crystals.

The present invention relates to a process for crystallization of dicarboxylic acids in a system, which is under continuous shear force that is created in the annular space between the impeller and the crystallizer wall. The system consists of selection and addition of additives in a manner to avoid any effect on the crystal purity.

To achieve the objectives of increased size, high purity and greater yield of crystals, in the present invention crystallization of diacids is carried out in a solution consisting of a solvent or a mixture of solvents, crude diacid and the additives in a crystallizer.

The crude diacids consists of one solute in major amount and impurities in minor amounts. When re-crystallized, the subject process provides a highly purified crystals of the diacids, as the amounts of impurities present, if any, are totally dissolved in the solvent/solution.

The solvents used in the present invention are selected preferably from water, any aliphatic monobasic acid having 2–4 carbons comprising primary and secondary hydrogen, any primary alcohol having 2–4 carbon or any combination thereof. Preferably, the solvent used in the subject process is water or water with small amount of acetic acid, wherein the ratio of water to acetic acid is more than 1:1. More preferably, the solvent with less than 10% of acetic acid is used. The preferred range of the solvent to the crude diacid is between 10 to 1 to 0.1 to 1. Most preferred range of the solvent to the crude diacid is 5 to 0.2

The additives used in the subject invention are selected from surfactants, and/or buffer salts and acid salts.

The surfactants addition results in obtaining bigger crystals with high purity. The surfactants are selected from non-ionic surfactants, anionic surfactants, cationic surfactants and zwifterionic surfactants. Preferably, the anionic surfactants are used. The preferred anionic surfactants can be selected from Sodium dodecyl sulfate (SDS), Sodium dodecyl benzene sulfonate (SDBS) and Sodium bis (2-ethyl hexyl) sulfosuccinate (AOT).

The nonionic surfactant used in the present invention are selected from hexoxy ethylene glycol mono-n-dodecyl ether ($C_{12}E_6$) and Tween 20.

The cationic surfactants can be selected from cetyl trimethyl ammonium bromide (CTAB) and dodecyl dimethyl ammonium bromide (DDAB).

The zwitterionic surfactants are selected from Phosphatidyl choline (PC) and Phosphatidyl ethanolamine (PE).

The amount of surfactants that is required for achieving good crystal size and shape is between 0.005% to 2.0% of the weight of the total solution. It has been observed that the concentration of surfactant below the critical micellar concentration (CMC) in the solution has achieved the desired results successfully. Most preferably, the amount of surfactant used is between 0.01% to 1.0% i.e. below the CMC.

To increase the yield of crystals the buffer acids and/or buffer salts are used as additives. The addition of salts results in increased rate of crystallization thus resulting in greater yield of crystals. The buffer salts exhibit resistance to the change in pH and acid salts increases the pH. The buffer salts used in the present process are selected from $Na_2HPO_4$, $NaH_2PO_4$, $KH_2PO_4$ and $K_2HPO_4$. Preferably these salts are selected from $Na_2HPO_4$ or $K_2HPO_4$ or a combination thereof. The amount of buffer salts taken is between 0.0025% to 1.0% of the weight of the total solution.

The acid salts used in the present invention are selected from $NaHSO_4$ and $KHSO_4$, more preferably $KHSO_4$. The amount of acid salts taken is between 0.0025% to 1.0% of the weight of the total solution.

Hence, in the subject crystallization process, both the acid and buffer salts along with the surfactants are used to achieve the desired average crystal size as surfactants makes the crystal grow and the salts precipitate out of the di-carboxylic acid.

The presence of surfactants results in growth of crystals, thereby results in obtaining crystals of higher purity. Salts present in the system results in the increased yield i.e. the weight of the crystals formed is more than the weight of crystals formed in a conventional process. The same is shown in the comparative table:

TABLE 1

|  | Conventional | with surfactant only (0.5% wt of solution) | with surfactant + salts 0.25 + 0.25% wt of solution | with salts only (0.5 % wt of solution) |
| --- | --- | --- | --- | --- |
| Yield (%) | 60.95 | 62.75 | 76.67 | 81.23 |
| Purity (%) | 99.8 | 100 | 99.92 | 99.8 |
| Time for crystallization (hrs) | 1.00 | 1.00 | 1.00 | 1.00 |
| Crystal size (microns) | 655 | 1814 | 1041 | 310 |

The amount of surfactants and buffer or acid salts is between 0.005% to 4.0% of the weight of the total solution.

As can be clearly seen from the Table-1, the presence of surfactants helps only in the growth of the crystals and the size of the crystal is increased by three times approximately. Increased size results in increasing the purity of crystals. Here, the yield increases but the increase is not considerable.

In case of the use of salts only as additives, the size of the crystals decreases, but the yield increases.

However, in the presence of both the salts and surfactants, there is increase in the yield, purity and size of the crystals.

In accordance with the present invention the diacid is crystallized in medium consisting of a suitable solvent, which is more preferably a mixture of water and acetic acid in different proportions and additives which are selected from surfactants, buffer salts or/and acid salts in a novel crystallizer having a impeller with impeller shaft.

In the process for the crystallization of di-carboxylic acid, the crude diacid at an acid value of 15–35, is put in the annular space, between the impeller and crystallizer wall. The crude diacid is dissolved in solvent at a suitable temperature at which the crude diacid is dissolved in the solvent to form a solution. The said solution is evaporated till a final acid value of 18–64 is achieved at a temperature of between 60–75° C. The resultant solution is then treated with additives and is cooled to 25–35° C. and crystallized for one hour, which results in the crystals of the di-acid to purge out of the solution which are later recovered by filtration/centrifugation.

BRIEF SUMMARY OF THE INVENTION

Accordingly, the subject invention relates to a process for the crystallization of di-carboxylic acids comprising: dissolving the crude dicarboxylic acid at a temperature between 30° C.–75° C. to dissolve the crude diacid in the solvent in an evaporator whereby portion of the said solvent evaporates increasing the concentration of the dicarboxylic acid in the said solution, transferring the said solution from the evaporator to a crystallizer, adding the additives selected from surfactant, buffer salts and/or acid salts or mixture thereof in the said evaporated solution in the said crystallizer, cooling the said mixture resulting in the formation of crystals of dicarboxylic acids, wherein the said crystallization takes place in the annular space between the impeller and the crystallizer wall at 10–80° C.

The present invention relates to a process for the crystallization of dicarboxylic acid comprising dissolving the crude dicarboxylic acid at a temperature between 30° C.–75° C. to dissolve the crude diacid in the solvent in an evaporator whereby portion of the said solvent evaporates increasing the concentration of the dicarboxylic acid in the said solution, transferring the said solution from the evaporator to a crystallizer, adding the additives selected from surfactant, buffer salts and/or acid salts or mixture thereof in the said evaporated solution in the said crystallizer, cooling the said mixture resulting in the formation of crystals of dicarboxylic acids, wherein the said crystallizer comprises solid cylindrical impeller conforming to the shape of the crystallizer rotated by means of cylindrical shaft attached to the speed motor, the said cylinder coaxial impeller or series of such impellers having different diameters separated from each other, and each of these cylinders moving at different speeds with the innermost impeller having the diameter between 3–5 cm, moving at highest speed preferably at the rate of 10–50 RPM and the outermost impeller having the diameter of between 5–10 cm, moving at lowest speed preferably at the rate of 1–10 RPM, rotated by a common shaft which is attached to the motor, wherein crystallization takes place in the annular space between the impeller and the crystallizer wall at 10–80 degrees C. maintaining the annular space between the two cylindrical impellers between 1 mm–50 cms.

The crystal forms are needle shaped, monoclinic crystals. The additives modifies the shape of crystal by increasing the leniency and decreasing the surface area.

Dissolution of the crude dicarboxylic acid in a solvent and the addition of additives in the said solvent can be carried in a separate evaporator out side the said crystallizer.

BRIEF DESCRIPTION OF THE ACCOMPANYING DRAWINGS

FIG. 1 depicts the diagram of the novel crystallizer

DETAILED DESCRIPTION OF THE INVENTION

The novel crystallizer used in the subject invention has a cylinder coaxial impeller (1) or series of impellers having different diameters separated from each other, moving at different speeds with the innermost impeller having the diameter between 5 cm to 3 meters, moving at highest speed preferably at the rate of 10–50 RPM and the outermost impeller having the diameter of between 5 cm to 10 meters, moving at lowest speed preferably at the rate of 1–10 RPM, rotated by a common shaft (3) which is attached to the motor. For these corresponding diameters of the innermost and the outermost impellers the corresponding annular space (2) between the two cylindrical impellers is between 1 mm to 50 cms.

The process of crystallization of dicarboxylic acid takes place in the annular space between the walls of cylindrical impellers. Since, the flow is unidirectional in the subject crystallizer, crystals are aligned in one direction. The surfactant molecules present in the said solution comes over the crystals, which results in increasing the size of the crystals. The crystals thus formed settle down due to the force of gravity.

The use of novel crystallizer of the subject invention as compared to the conventionally available crystallizer has found to give better yield, high purity, increased crystal size and reduced time used for crystallization, as shown in the comparative Table 2.

TABLE 2

|  | Conventional | Novel Crystallizer of the subject invention |
|---|---|---|
| Yield (%) | 60.95 | 61.45 |
| Purity (%) | 99.8 | 99.8 |
| Time for crystallization in minutes | 60 | 40 |
| Crystal size in microns | 655 | 710 |

Table-2

The newly designed impeller used in the present invention helped in relatively increasing the rate of crystallization and growth of crystals over conventional crystallization processes. The crystals that are formed in the top part of the crystallizer fall down rapidly due to the force of gravity. Crystals are continuously removed from time to time if the process is continuous and are allowed to stay at the bottom of the crystallizer if the process is in batch mode.

To achieve the faster crystallization rate the specially designed impeller is used. The criticality of the inventive part of the crystallizer resides in the gap i.e. annular space between the impeller and the wall of the crystallizer. The annular space between the agitator and the crystallizer is maintained be between 2 cms to 100 cms.

The subject invention can be best illustrated by way of following examples.

EXAMPLES 1–5

Example 1

Crystallization of crude succinic acid is carried out in an annular space between the impeller and crystallizer wall. 10 gms of crude succinic acid (around 98% pure) is initially taken with an acid value of 18.37. The solvent is water. The additives are introduced. The amount of surfactant, sodium laurl sulfate is 0.5% of the crude acid weight. The percentage of acid salts is 0.5% of the crude acid weight. The salts taken is $KHSO_4$. The solution is evaporated till a final acid value of 20.132 is reached. The temperature of evaporation is 65° C. The system is then cooled to around 32° C. and crystallized in the novel crystallizer for 1 hr. The solution is then filtered and dried. A total yield of 72.014% of highly pure succinic acid is obtained. The amount of impurities are less than 100 ppm. The average size of the crystals is 996 microns. The conventional process gave a yield of 52.36% of lesser purity. The average size of the crystals in conventional process was 514 microns.

Example 2

Crystallization of crude succinic acid is carried out in an annular space between the impeller and crystallizer wall. 10 gms of crude succinic acid (around 98% pure) is initially taken with an acid value of 20. The solvent is water. The additives are introduced. The amount of surfactant, sodium laurl sulfate is 1.0% of the total diacid weight. The percentage of acid salts is 1.0% of the total diacid weight. The salts taken is $KHSO_4$. The solution is evaporated till a final acid value of 30 is reached. The temperature of evaporation is 65° C. The system is then cooled to around 28° C. and crystallized in the novel crystallizer for 1 hr. The solution is then filtered and dried. A total yield of 83.66% of highly pure succinic acid is obtained. The amount of impurities are less than 150 ppm The average size of the crystals is 1151 microns. The conventional process gave a yield of 58.36% of lesser purity( 99.12%). The average size of the crystals in conventional process was 506 microns.

Example 3

Crystallization of crude oxalic acid is carried out in an annular space between the impeller and crystallizer wall. 10 gms of crude oxalic acid (around 98% pure) is initially taken with an acid value of 30.04, in a mixture of water (90% by volume) and acetic acid (10% by volume). Sodium laurl sulfate in an amount of 1.0% of the total solution weight is added along with acid salts in an amount of 1.0% of the total weight of the solution. The salts taken are a mixture of $KHSO_4$ and $K_2HPO_4$. The solution is evaporated till a final acid value of 52.62 is reached. The temperature of evaporation is 65° C. The system is then cooled to around 30° C. and crystallized in the novel crystallizer for 1 hr. The solution is then filtered and dried. A total yield of 78.86% of highly pure succinic acid is obtained. The amount of impurities are less than 50 ppm and the average crystal size obtained is 998 microns.

Example 4

Crystallization of crude Adipic acid is carried out in an annular space between the impeller and crystallizer wall. 6.034 gms of crude Adipic acid is initially taken with an acid value of 30.04 and the purity of 66.7% in water. Sodium laurl sulfate in an amount of 1.0% of the total solution weight is added along with acid salts in an amount of 1.0% of the total weight of the solution. The salt taken is $Na_2HPO_4$. The solution is evaporated till a final acid value of 60.62 is reached. The temperature of evaporation is 73° C. The system is then cooled to around 30° C. and crystallized in the novel crystallizer for 1 hr. The solution is then filtered and dried. A total yield of 89.22% of highly pure oxalic acid is obtained. The amount impurities are less than 50 ppm. The average crystal size obtained is 880 microns.

Example 5

Crystallization of crude Adipic acid is carried out in an annular space between the impeller and crystallizer wall. 5.006 gms of crude succinic acid (around 98% pure) is initially taken with an acid value of 16.583. The solvent is water. The additives are introduced. The amount of surfactant, sodium dodecyl sulfate is 0.5% of the crude succinic acid weight. The weight percentage of salts is 0.5% of the crude succinic acid weight. The salts taken is $KHSO_4$. The solution is evaporated till a final acid value of 20 is reached. The temperature of evaporation is 65° C. The system is then cooled to around 28° C. and crystallized in the novel crystallizer for 1 hr. The solution is then filtered and dried. A total yield of 72.78% of highly pure succinic acid is obtained. The amount of impurities are less than 100 ppm. The average size of the crystals is 1008 microns. The conventional process gave a yield of 52.36% of lesser purity. The average size of the crystals in conventional process was 514 microns.

The subject process is a mere statement of invention and should not in any way construed to restrict the scope of the invention.

We claim:

1. A process for the crystallization of dicarboxylic acids comprising recrystallizing a solution of crude dicarboxylic acid in a crystallizer in the presence of at least one additive selected from the group consisting of surfactants, buffer salts, acid salts or a mixture thereof, wherein the crystallizer comprises a series of cylindrical impellers, a crystallizer wall and a rotatable impeller shaft, wherein an annular space is formed between the impellers and crystallizer wall, said crystallization being effected while rotating the cylindrical impellers in a unidirectional flow with the solution of crude dicarboxylic acid that creates a velocity gradient which forms, upon cooling, crystals of dicarboxylic acids in the annular space at 10° C. to 80° C. that are sheared, elongated and increased in size.

2. A process as claimed in claim 1, wherein the crystallizer comprises a series of such impellers hating different diameters separated from each other conforming to the shape of the crystallizer, and each of these impellers move at different speeds with the innermost impeller having a diameter between about 0.05 m to about 3 m, moving at a rate of 10 to 50 RPM and the outermost impeller having a diameter between 0.05 m to 10 m, moving at a lower speed than the inner impeller at the rate of 1 to 10 RPM, the impeller or series of impellers being rotated by a common gear shaft driven by motor.

3. A process as claimed in claim 2, wherein the space between the series of impellers is between 0.01 cm to 50 cm.

4. A process as claimed in claim 1, wherein said solution comprises a solvent selected from the group comprising water, any aliphatic monobasic acid having 2–4 carbons, wherein the monobasic acid has a primary or secondary hydrogen such as acetic acid, any primary alcohol having 2–4 carbons or any combination thereof.

5. A process as claimed in claim 4, wherein the solvent is a mixture of water and acetic acid in the ratio greater than 1:1 by weight.

6. A process as claimed in claim 4, wherein the solvent comprises less than 10% by weight of acetic acid.

7. A process as claimed in claim 1, wherein a surfactant is present and said surfactant is selected from a group comprising anionic surfactants, non-ionic surfactants, cationic surfactants and zwitterionic surfactants.

8. A process as claimed in claim 7, wherein the anionic surfactant is selected from sodium dodecyl sulfate (SDS), sodium dodecyl benzene sulfonate (SDBS) and sodium bis (2-ethyl hexyl) sulfosuccinate (AOT).

9. A process as claimed in claim 7, wherein the nonionic surfactant is selected from hexoxy ethylene glycol mono-n-dodecyl ether ($C_{12}E_6$) and polysorbates.

10. A process as claimed in claim 7, wherein the cationic surfactant is selected from cetyl trimethyl ammonium bromide (CTAB) and dodecyl dimethyl ammonium bromide (DDAB).

11. A process as claimed in claim 7, wherein the zwitterionic surfactant is selected from phosphatidyl choline (PC) and phosphatidyl ethanolamine (PE).

12. A process as claimed in claim 1, wherein the solution is cooled to a temperature of between 28° C. to 32° C.

13. A process as claimed in claim 1 wherein prior to crystallization the solution of crude diacid is evaporated to have a final acid value of 18 to 64 at a temperature between 60° C. to 75° C.

14. A process as claimed in claim 1, wherein the annular space between the impellers and the crystallizer wall has a width of 10 to 60 cm.

15. A process as claimed in claim 7, wherein the anionic surfactants are in the range of 0.005% to 2.0% of the weight of the solution.

16. A process as claimed in claim 1, wherein the annular space between the impellers and the crystallizer wall has a width 2 to 100 cm.

17. A crystallizer used for crystallizing dicarboxylic acids comprising:
    a series of cylindrical impellers;
    a crystallizer wall;
    a rotatable impeller shaft; and
    an annular space between the cylindrical impellers and the crystallizer wall, wherein the series of cylindrical impellers have different diameters separated from each other and each of these impellers move at different speeds rotated by a common gear shaft to crystallize the dicarboxylic acid by rotating the cylindrical impellers in a unidirectional flow to create a velocity gradient which forms, upon cooling, crystals of dicarboxylic acids in the annular space that are sheared, elongated and increased in size.

18. A process as claimed in claim 1, wherein said velocity gradient and unidirectional flow are enhanced by use of a series of impellers moving at different speeds with the innermost impeller moving at the fastest speed.

* * * * *